(12) United States Patent
Benner et al.

(10) Patent No.: US 9,936,871 B2
(45) Date of Patent: Apr. 10, 2018

(54) NON-SLIDING AND NON-SUTURED CONTACT LENS SYSTEM FOR OPHTHALMIC PROCEDURES

(71) Applicant: DRUG DELIVERY COMPANY, LLC, Salisbury, MD (US)

(72) Inventors: Jeffrey D. Benner, Salisbury, MD (US); Steven M. Cohen, Saint Petersburg, FL (US); Christopher Forrest Lumpkin, Evergreen, CO (US)

(73) Assignee: Drug Delivery Company, LLC, Salisbury, MD (US)

( * ) Notice: Subject to any disclaimer, the term of this patent is extended or adjusted under 35 U.S.C. 154(b) by 0 days.

(21) Appl. No.: 15/497,827

(22) Filed: Apr. 26, 2017

(65) Prior Publication Data

US 2017/0311801 A1    Nov. 2, 2017

Related U.S. Application Data

(60) Provisional application No. 62/329,292, filed on Apr. 29, 2016.

(51) Int. Cl.
  *A61B 3/00* (2006.01)
  *A61B 3/125* (2006.01)
  (Continued)

(52) U.S. Cl.
  CPC .............. *A61B 3/125* (2013.01); *A61B 3/117* (2013.01); *A61B 17/0231* (2013.01); *A61B 2017/00946* (2013.01)

(58) Field of Classification Search
  CPC ..... A61B 3/117; A61B 3/125; A61B 17/0231; A61B 17/00946; A61F 9/009; A61F 9/00736; A61F 9/0017; A61F 9/00821; A61F 9/00781; B65D 75/22; A61N 5/1017; A61N 5/103; A61N 5/1037; G02C 7/04; G02C 7/049; G02B 5/04
  (Continued)

(56) References Cited

U.S. PATENT DOCUMENTS 5,479,222 A    12/1995   Volk
5,963,301 A    10/1999   Volk
(Continued)

OTHER PUBLICATIONS

Overview of "Ocular Vitrectomy Lens Rings" from Ocular Instruments, Inc.
(Continued)

*Primary Examiner* — Mustak Choudhury
(74) *Attorney, Agent, or Firm* — Rosenberg, Klein & Lee

(57) ABSTRACT

A non-sliding, non-sutured hands-free contact lens assembly for ophthalmic procedures utilizes a number of microstructures strategically placed on the bottom of either the contact lens or the bottom of a contact lens holder ring. After the contact lens, or the contact lens assembled with the contact lens holder ring, is placed on the cornea of the eye and centered, a surgeon applies downward pressure either on the contact lens itself or on the lens holder ring. This secures the lens assembly to the cornea due to increased friction between the microstructures and the tissues of the eye when the microstructures penetrate through the tear film and, optionally, viscous solution film and into the contact with superficial layer of cornea or other parts of the eye, thus temporarily anchoring the contact lens, or lens holder, to the desired surgical site.

24 Claims, 12 Drawing Sheets

(51) Int. Cl.
*A61B 3/117* (2006.01)
*A61B 17/02* (2006.01)
*A61B 17/00* (2006.01)

(58) Field of Classification Search
USPC .......... 351/205, 206, 219, 246, 218, 159.02,
351/159.04; 378/65; 600/209, 236;
623/1.11, 4.1, 5.16, 5.11; 606/4, 5, 10,
606/107
See application file for complete search history.

(56) References Cited

U.S. PATENT DOCUMENTS

| | | | |
|---|---|---|---|
| 6,120,147 A | | 9/2000 | Vikfvinkel et al. |
| 8,070,290 B2 | | 12/2011 | Gille et al. |
| 9,339,184 B2 | | 5/2016 | Hassan et al. |
| 2009/0161826 A1 | * | 6/2009 | Gertner ................ A61N 5/1017 378/65 |
| 2010/0036488 A1 | | 2/2010 | de Juan, Jr. et al. |
| 2012/0099077 A1 | * | 4/2012 | Abt ........................ A61B 3/125 351/219 |
| 2015/0153588 A1 | | 6/2015 | Angelini et al. |
| 2015/0327764 A1 | | 11/2015 | Graham et al. |

OTHER PUBLICATIONS

International Search Report From Counterpart PCT Application dated Sep. 15, 2017.

* cited by examiner

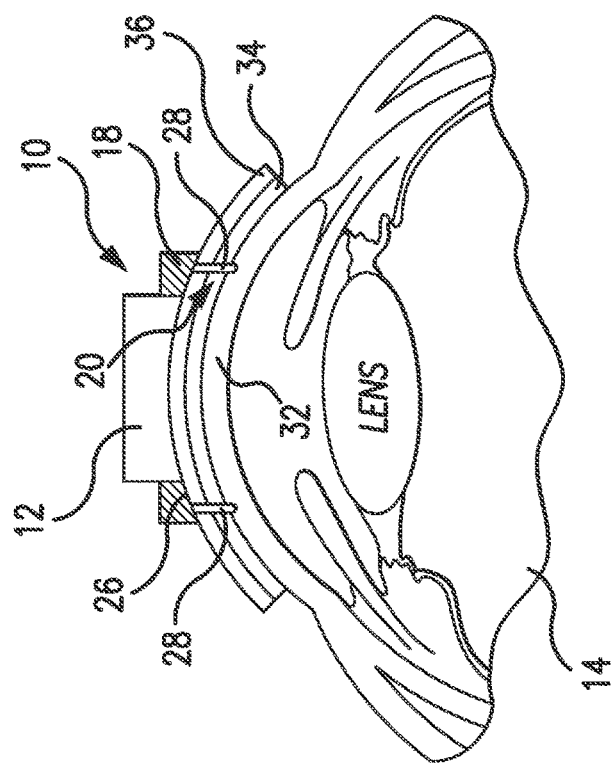
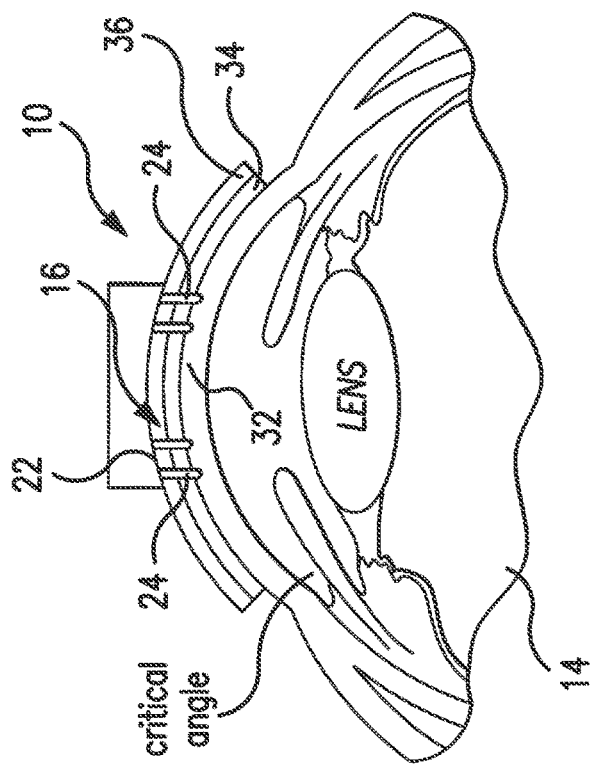

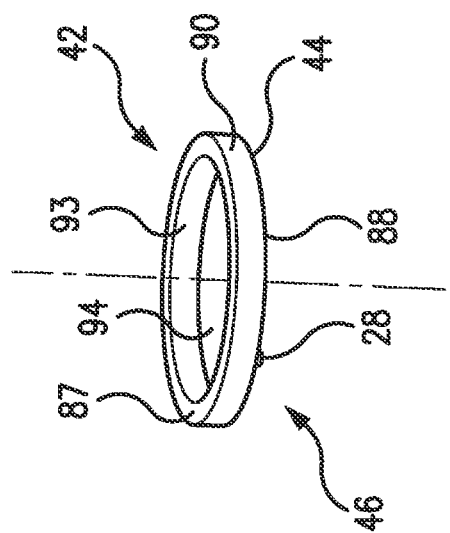
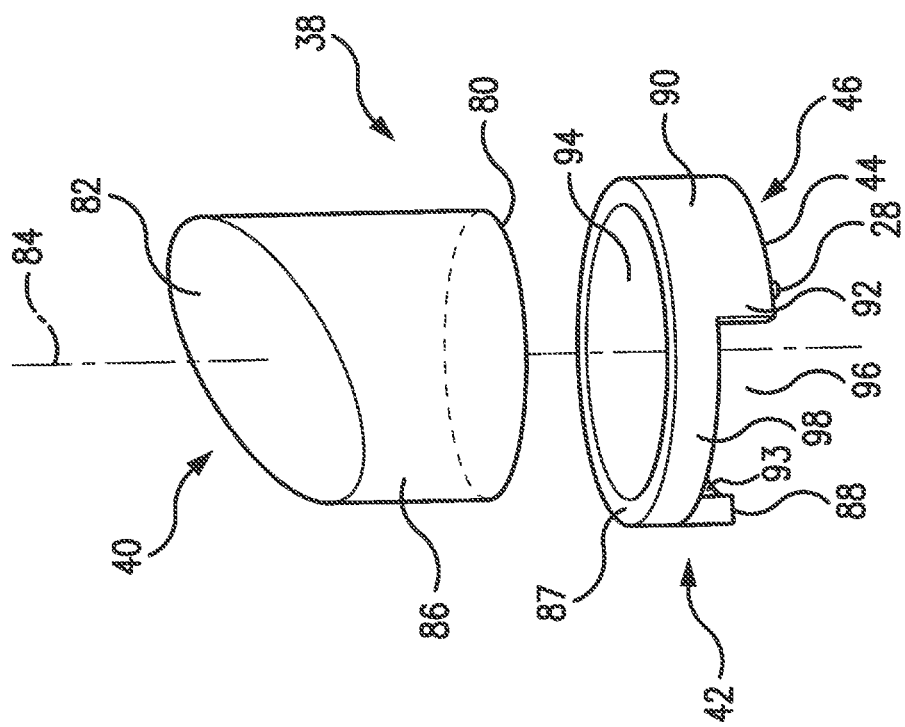
FIG. 7A
FIG. 6A

NON-SLIDING AND NON-SUTURED CONTACT LENS SYSTEM FOR OPHTHALMIC PROCEDURES

RELATED APPLICATIONS

This Application is based upon Provisional Patent Application Ser. No. 62/329,292 filed on 29 Apr. 2016.

FIELD OF THE INVENTION

The present invention is directed to the field of ophthalmic surgical intervention, and particular to contact lens used in ophthalmic surgeries.

More in particular, the present invention is directed to corneal (and macular) contact lenses, as well as gonioprisms, used in vitreoretinal surgeries (procedures), which allow a surgeon to visualize the macula and other structures of the eye under surgery at high magnification.

In addition, the present invention is directed to contact lenses used in ophthalmic procedures which are configured with an anchoring mechanism which stabilizes and centers the lens on the cornea of the eye (or other desired site of procedure) in a "hands-free" manner without the need for monitoring and manual positioning of the contact lens during ophthalmic procedures.

Further, the subject system is directed to a contact lens anchoring system which does not require suturing for stabilization and centration during the ophthalmic procedure, and thus is free of superficial bleeding from the conjunctiva caused by the suturing.

The present invention is further directed to a non-sutured and hands-free contact lens anchoring system for ophthalmic surgeries which effectively stabilizes and centers the lens on the cornea of the eye during surgery and which is prevented from sliding on the area of interest by a number of microstructures strategically placed on the bottom of either the contact lens itself or the bottom of a non-sutured contact lens holder. The microstructures are gently pressed down into contact with the superficial layer of the eye tissue during the surgery, thus temporarily anchoring the contact lens to the cornea and are easily removed (or lifted away) from the eye when the procedure is completed.

Additionally, the present system is directed to a suture free, non-sliding stabilization anchoring system for a corneal (or macular) contact lens, as well as gonioprism contact lens, used in vitreoretinal surgeries, which is configured with microstructures located on the bottom of either the contact lens or the contact lens holder, and which gently indent into the superficial cornea during the procedure to temporarily anchor the contact lens or lens holder to the cornea without injuring the eye tissues.

BACKGROUND OF THE INVENTION

Corneal contact lenses are a critical part of vitreoretinal surgery, especially macular surgery. The contact lenses allow a surgeon to visualize the macular as well as other structures of the eye at high magnification. Surgeons typically employ a separate lens that can be placed directly on the eyeball and allow focusing to be extended to the retina and other areas in the back of the eyeball.

In order to be effective, a contact lens must be stably positioned and centered on the cornea of the eye at the site of the surgery. This is difficult to achieve due to the cornea curved contouring. The slipperiness is made worse by the use of viscous coupling agents (such as, for example, viscoelastics or hydroxymethyl cellulose), which are used to avoid bubble formation beneath the contact lens during the surgery.

The lens placed on the eyeball floats on a thin layer of fluid and tends to slide about the surface of the eye. In order to overcome the sliding displacement and to hold the lens in place, a surgeon or a surgeon's assistant constantly monitors the lens position and uses a rod or other extension (handle) to push the lens back to a desired location. In order to perform this task, the surgeon or surgeon's assistant must have a profound experience in vitreoretinal surgery which is not always the case.

For example, U.S. Pat. No. 5,070,290, describes the gonioscopy, which is a technique used for viewing inner portions (such as the retina and the anterior chamber angle) of the eye for evaluation, management, and classification of normal and abnormal structures of the eye. The gonioscopy technique uses devices known as gonioscopes to enhance visibility of the trabecular meshwork and anterior chamber angle during surgical procedures. The gonioscope is handheld by a surgeon in place over the patient's cornea while he/she performs the surgical procedure.

The gonioscope described in U.S. Pat. No. 8,070,290 includes the Hill gonioprism positioned on a patient's eye. The gonioscopic optical element, which includes one or several lens, such as optical prism(s), is received in a lens retainer, and a handle or a grip is attached to the lens retainer. During the surgical procedure, the gonioscopic optical element is positioned over or on the patient's eye, e.g. the cornea of the eye.

A light source is used during the surgery which emits light toward the patient's eye. The light source may be configured such that light from the source illuminates the patient's eye, the anterior chamber, and the eye structures near the anterior chamber, e.g. trabecular meshwork, such that one or more of these structures reflect(s) light incident from the light source.

The light source and the prism(s) is (are) arranged in such a fashion that the light from the light source is reflected by the patient's eye (or specific optical structures), traverses the gonioscopic prism(s), and is redirected, e.g., refracted and diffracted, by the gonioscopic prisms. An image is formed of at least part of the patient's eye and this image is viewed using a microscope.

The handle of the gonioscope described in '290 patent is used to stabilize and centralize the entire gonioscope structure. This arrangement generally requires assistance of a surgeon assistant to manipulate the handle of the gonioscope during the procedure.

Landers has improved upon the gonioscope prism requiring manual manipulation of the handle during the ophthalmic procedure surgery, and provided a "hand-free" solution for the problem which eliminates the need for a surgeon assistant to manually stabilize and centralize the contact lens.

The Landers' system uses a lens ring which circumferentially envelopes sides of the contact lens, and serves as the lens holder. To stabilize and centralize the contact lens at the desired site during the procedure, the lens ring is secured to the conjunctiva/sclera with a pair of fixation sutures. The contact lens is placed inside the lens ring which remains in place by the fixation sutures, and thus, the contact lens is maintained in place and sutured throughout the duration of the macular surgery.

Fixation sutures, however, are not welcomed by a majority of ophthalmologists, especially glaucoma surgeons, due to traumatic effects of the fixation sutures to the cornea or sclera of the eye. In addition to the traumatic nature of the fixation sutures (which typically cause bleeding which can obscure view of the surgical site), if the sutures are excessively tight, the cornea can be disturbed and the sutures may break during the surgery, which is definitely a disadvantage of the suturing approach. On the other hand, if the sutures are too loose, the displacement of lens may occur, which can undermine the surgery efficiency.

Since the Landers development, various solutions for "suture-less" contact lens stabilization have been developed. For example, as presented in U.S. Pat. No. 5,963,301, the lens is constructed with a flange that is shaped to conform to the general curvature of an average eye. In order to be attached to the eye surface, and thus stabilizing the lens in place, the flange is formed with a number of peripheral openings or recesses sized to accommodate various types of instruments to be inserted into the eye during the surgery. The flange is formed with fittings to which a vacuum is applied in order to pull the flange into contact with the sclera of the eye by creating a vacuum between the flange and eye to enhance holding the lens device in position.

Another method for overcoming the problem of contact lens movement during surgery is disclosed in U.S. Pat. No. 6,120,147 where the lens are replaced with flexible lens having a relatively flexible flange which is fixed in place by capillary action.

U.S. Patent Application Publication No. 2014/0307229 and related U.S. Pat. No. 9,339,184 describe a contact lens for vitreoretinal surgery where a contact lens assembly has a central lens and a circumscribing flange. The lens has an eye contact surface shaped generally to a radius of curvature of a cornea of an eye. The flange comprises a sterile sponge-like liquid absorbent flexible material having a central aperture for fitting snuggly about an outer circumference of the lens and extending radially outward therefrom.

During the procedure, the lens is mated with a flange and the lens/flange assembly is then placed on the wetted eye of a patient. Additional wetting compound, such as sterile saline solution, is then spread onto the flange until the flange is generally situated. The lens can then be moved as necessary for viewing and the wetted flange holds the lens in a desired position.

It has been found that most of the prior art devices slide off of the cornea during the surgery. The surgeon, or the surgeon's assistant, must push the lens back to the center of the cornea a number of times during critical steps of the surgery. This may cause loss of the surgical field at a crucial moment. Thus, the suture-less systems currently available, are not preferred by many surgeons. The surgeons use the sutured lens ring even though it takes additional time and causes superficial bleeding from the conjunctiva.

It is highly desirable to provide a suture-free and hands-free non-sliding corneal contact lens stabilization and anchoring system for vitreoretinal surgery which does not require monitoring and manual positioning of the lens during the surgery and which provides hands-free effective stabilization and centralization of the lens during a surgical procedure in trauma-free manner.

One of the important topics discussed among glaucoma surgical specialists is micro invasive glaucoma surgery, further referred to herein as MIGS. The MIGS refers to a group of relatively recent glaucoma surgery techniques that are gentler and involve less tissue disruption than traditional glaucoma surgeries (such as trabeculectomy and shunts).

The glaucoma specialists indicate that there is a significant learning curve in order to master MIGS technique. Operating directly on the tiny trabecular meshwork is challenging. Obtaining visualization of the angle is the most difficult part of the learning curve and the key to mastering this surgery. The critical angle of the peripheral cornea may cause total internal reflectivity of light. For that reason, special contact lenses are needed to allow visualization of the angle structures.

Even with a surgical gonioprism, the critical angle surgery is difficult to perform. Mastering the usage of the current surgical gonioprism is a significant barrier for many surgeons. In order to visualize the angle structures, a surgeon rotates the patient's head to the side by 30°, to the microscope 30°, and to steady a hand-held surgical gonioprism on the cornea with their non-dominant hand (as shown, for example, in U.S. Pat. No. 8,070,290). This requires a significant amount of practice and steady hands. The surgeon cannot learn the technical steps of the MIG surgery, such as implanting the stent or cutting into the trabecular meshwork, until they can consistently obtain a steady view of the angle.

Glaucoma surgeons are universally opposed to placing fixation sutures. They do not want to cause any trauma to the cornea or sclera of the eye. Simplifying and improving the visualization of the critical angle during the surgery, without causing tissue injury by fixating sutures can remove the barriers that are currently limiting adoption of this newest type of glaucoma surgery, i.e., MIGS.

It is highly desirable to provide a device/system for vitreoretinal surgery where the contact lens can be stabilized and centralized over the surgical area of the eye in a suture free non-sliding manner without the need for manual repositioning and centralization of the contact lens during the operation.

SUMMARY OF THE INVENTION

It is therefore an object of the present invention to provide a contact lens assembly for ophthalmic procedures which would attain a non-sliding non-sutured hand-free operation for the lens stabilization and centralization during a vitreoretinal surgery.

It is another object of the present invention to provide a contact lens assembly equipped with an anchoring system capable of hands-free stabilization and centralization of the contact lens assembly at a desired site of procedure in a non-sutured trauma-reduced manner.

In one aspect, the present invention is directed to a contact lens assembly for ophthalmic procedures, which comprises an optical element (such as a contact lens) and an anchoring mechanism formed on the eye contact surface. The anchoring mechanism is configured with microstructures disposed at predetermined positions on the eye contact surface of the optical element, and creates an anchoring action for the optical element at a desired procedure site when the microstructures are brought in contact with tissues of the eye during an ophthalmic procedure. Specifically, during the ophthalmic procedure, the optical element is placed on the desired procedure site with the microstructures in contact with superficial layer of the eye cornea.

The microstructures of the anchoring mechanism may have different forms, and may include, for example, micro-pins, micro-grips, micro-barbs, micro-needles, textured micro-elements, etc., and combinations thereof, with the important consideration being that they provide a friction force between the contact lens assembly and the eye's tissues.

The microstructures of the anchoring mechanism extend from the eye contact surface of the optical element a length not exceeding 1 mm in order to prevent a deep penetration in the eye's tissues.

The microstructures may be attached to the eye contact surface by numerous means, such as, for example, threaded connection, adhesion, gluing, pressing, thermo-soldering, 3-D printing, etc., and combinations thereof.

The microstructures may be formed from surgical steel, polyether ether ketone (PEEK) polymer, various bio-compatible plastics, and combinations thereof.

In another aspect, the present invention is directed to a contact lens assembly for ophthalmic procedures, which comprises an optical element (which may be a corneal contact lens, as well as a gonioprism contact lens) having a bottom eye contact surface, an upper surface, and side walls extending circumferentially between a peripheral edge of the bottom eye contact surface and a peripheral edge of the upper surface.

The contact lens assembly further includes an annularly contoured optical element holder having an annularly shaped bottom surface, an annularly shaped upper surface, and outer walls extending circumferentially along and between outer edges of the annularly shaped bottom and upper surfaces, respectively, of the annularly contoured optical element holder.

The annularly contoured optical element holder further has internal walls extending circumferentially along and between inner edges of the annularly shaped bottom and upper surfaces, respectively, of the annularly contoured optical element holder. The internal walls of the annularly contoured optical element holder define a holder opening which is shaped and dimensioned in correspondence to the bottom eye contact surface of the optical element.

An anchoring mechanism is formed on the annularly shaped bottom surface of the annularly contoured optical element holder. The anchoring mechanism is configured with microstructures disposed at predetermined positions on the bottom surface of the annularly contoured optical element holder to create an anchoring friction force between the bottom surface of the annularly contoured optical element holder and the eye tissues to stabilize and centralize the contact lens assembly at a desired procedure site by bringing the microstructures in contact with tissues of the eye during an ophthalmic procedure.

During the ophthalmic procedure, the optical element is received in the holder opening of the annularly contoured optical element holder and is maintained with the bottom eye contact surface in contact with the tissues of the eye at the desired procedure site by the annularly contoured optical element holder anchored at the desired procedure site through the action of the anchoring mechanism formed on the bottom surface of the annularly contoured optical element holder.

The microstructures of the anchoring mechanism may be in numerous forms, including, for example, micro-pins, micro-grips, micro-barbs, micro-needles, textured microelements, etc., and combinations thereof, positioned at strategic locations on the bottom surface of the optical element holder.

The microstructures of the anchoring mechanism extend from the eye contact surface of the optical element a length not exceeding 1 mm in order to prevent deep penetration in the eye's tissues.

The microstructures are attached to the eye contact surface of the optical element holder by any of the mechanisms including, for example, threaded connection, drilling, adhesion, gluing, pressing, thermo-soldering, 3-D printing, etc., and combination thereof.

The walls of the annularly contoured optical element holder may be shaped with a cut-out portion extending a predetermined length (partially or along the entire perimeter) along the walls for surgical tool access and visualization of the desired procedure site.

The annularly contoured optical element holder may be manufactured from surgical steel, or polyether ether ketone (PEEK) polymer, or other bio-compatible polymers and plastics. The holder opening may have a diameter ranging from 9 mm to 14 mm, and specifically, for example, approximately 11.5 mm.

The optical element further includes a flange member formed on the side walls thereof and extending circumferentially along the perimeter of the side walls. A flange portion of the flange member extends from the side walls surface a predetermined distance corresponding to a width of the annularly shaped upper surface between the inner and outer edges thereof. During the ophthalmic procedure, the optical element is received in the holder opening with the flange portion positioned in contact with and supported by the annularly shaped upper surface of the annularly contoured optical element holder to restrict a downward displacement of the optical element relative to the annularly contoured optical element holder.

In another embodiment, the annularly contoured optical element holder and the optical element may be assembled together with a bonding agent (such as glue) or an interlocking tab and groove locking mechanism.

Further, there is provided a stabilization system for maintaining a contact holder lens and contact lens in a stabilized and secure position during an ophthalmic procedure when the patient tilts or inclines his/her head to negate gravity assist effects caused by the head inclining or tilting.

Still further, there is provided a contact lens assembly for opthlalmic procedures which includes an eye speculum secured with, and operationally operative with the stabilization mechanism which is secured to the lens and/or lens holder to stabilize the contact lens at a predetermined positional location during the ophthalmic procedure.

Still further there is provided a stabilizing mechanism used in conjunction with an eye speculum which has an anchoring mechanism for retaining the contact lens at a selected procedure site during the ophthalmic procedure. The stabilizing mechanism includes a plurality of microstructures located on a bottom surface of the contact lens and/or a bottom surface of the contact lens holder which is in contact with the eye of the patient during the ophthalmic procedure.

In still another aspect, the present invention is directed to a method for performing an ophthalmic procedure with the use of the non-sliding non-sutured, hands-free contact lens anchoring system.

The method includes the steps of:
configuring a contact lens assembly comprising:
(a) a contact lens having a bottom eye contact surface, an upper surface, and sidewalls extending circumferentially between an edge of the bottom eye contact surface and an edge of the upper surface,
(b) an annularly contoured lens holder having:
an annularly shaped bottom surface,
an annularly shaped upper surface,
outer walls extending circumferentially along and between outer edges of said annularly shaped bottom and upper surfaces of its annularly contoured lens holder, internal walls extending circumferentially along and between inner edges of the annularly shaped bottom and upper surfaces of the annularly contoured lens holder and defining a holder opening therebetween. The holder opening being shaped and dimensioned in correspondence to the bottom eye contact surface of the lens, and (c) an anchoring mechanism formed on either the bottom eye contact surface of the lens, or on the annularly shaped bottom surface of the annularly contoured lens holder, where the anchoring mechanism is configured with microstructures creating an anchoring action for the lens at a desired procedure site when the microstructures are brought in contact with tissues of an eye under an ophthalmic procedure.

The method continues with the steps of:

placing the contact lens assembly to the desired procedure site;

pressing the contact lens assembly downward to attain contact between the microstructures and the tissues of the eye under the ophthalmic procedure;

performing the ophthalmic procedure; and upon completion of the ophthalmic procedure, lifting the contact lens assembly from the eye.

Another aspect of the subject invention is in the provision of contact lens assembly for maintaining the contact lens at a predetermined relatively fixed position during the ophthalmic procedure which includes the combination of an eye speculum and a stabilization mechanism secured to the eye speculum.

In this aspect of the subject invention, the stabilizing mechanism includes a stabilizing wire which on a lower end is fixedly attached to opposing sides of a contact lens holder and at an upper end is secured to a plate member of the eye speculum. The stabilizing wire may be formed of a malleable but somewhat resilient composition. An upper end or section of the stabilizing wire is secured to the plate member by a pair of sleeve members having appendages which may be frictionally secured to the plate member.

These and other objects of the present invention will be apparent when reviewed in conjunction with accompanying Patent Drawings in the subject Patent Application and the description of the preferred embodiments.

BRIEF DESCRIPTION OF THE DRAWINGS

FIGS. 1A-1B are schematic representations of the subject contact lens (FIG. 1A) and contact lens holder/assembly (FIG. 1B) attached to the cornea of the eye during the surgical procedure;

FIG. 3A is a view of the subject lens from the bottom, and FIG. 4A is a side view of the subject contact lens, showing microstructures placed on the bottom of the contact lens;

FIG. 3B is a bottom view of the lens holder assembly, and FIG. 4B is a side view of the subject lens/holder assembly;

FIGS. 6A-6B show an exploded view of the gonioprism contact lens assembly, where FIG. 6A is a side view and FIG. 6B is a bottom view of the subject gonioprism contact lens assembly;

FIGS. 7A-7B show a side view (FIG. 7A) and a bottom view (FIG. 7B) of the subject gonioprism lens holder in an alternative embodiment;

DETAILED DESCRIPTION OF THE PREFERRED EMBODIMENTS

Figure 2:
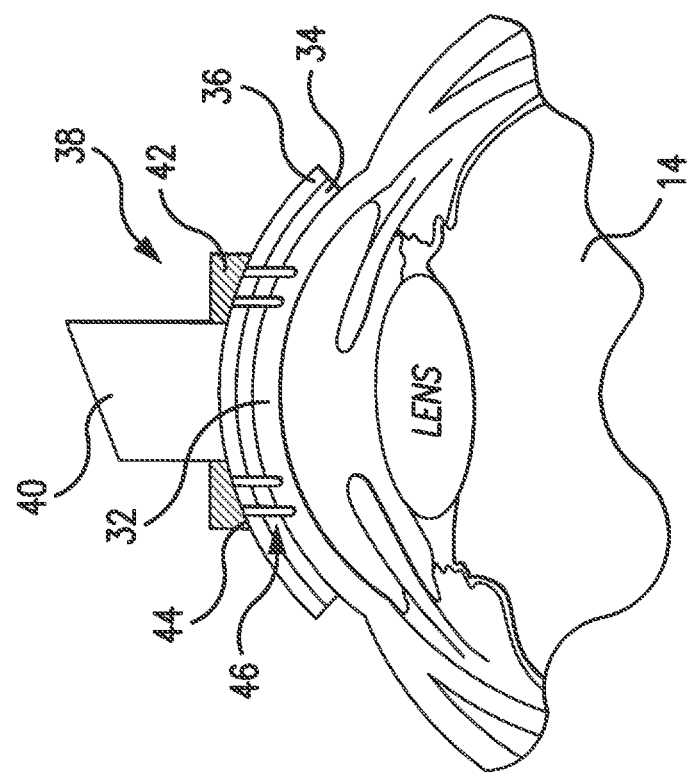
FIG. 2 is a schematic representation of the subject gonioprism contact lens assembly attached to the eye during the surgical procedure.

FIGS. 1A and 1B show schematically the anchoring of the subject suture-free, non-sliding corneal contact lens assembly on the eye during an ophthalmic procedure. As shown in FIG. 1A, the subject cornea contact lens assembly 10 includes a contact lens 12 removeably attached to the eye 14 by means of anchoring system 16 (which will be detailed in further paragraphs). Alternatively, as shown in FIG. 1B, the subject contact lens assembly 10 for ophthalmic procedures includes the contact lens 12 and the contact lens holder 18 which receives the lens 12 and holds the entire system 10 in place during the ophthalmic procedure through the action of the anchoring system 20 on the bottom of the contact lens holder 18.

As shown in FIG. 1A, the anchoring system 16 is formed on the bottom 22 of the contact lens 12 in the form of microstructures 24 which, when brought into contiguous contact with the eye 14, secure the contact lens 12 in place for the duration of the ophthalmic procedure.

As shown in FIG. 1B, the anchoring system 20 is configured on the bottom 26 of the contact lens holder 18. The anchoring system 20 is formed with microstructures 28 which, when brought in contiguous contact with the tissues of the eye 14, maintain the contact lens holder 18 in position during the ophthalmic procedure, and thus supports the contact lens 12 at the desired site of operation.

The system 10 is a novel non-sliding corneal contact lens assembly equipped with the suture-free stabilization/anchoring system for vitreoretinal surgery which utilizes the microstructures 24 on the bottom 22 of the lens 12 or the microstructures 28 on the bottom 26 of the ring holder 18. Microstructure 24 may be in numerous shapes, including, for example, micro-pins 30, micro-grips, micro-barbs, micro-needles, or other textured microstructures on the bottom surface of the contact lens 12 or the contact lens holder 18.

For the sake of simplicity and clarity of description, the microstructures 24 and 28 are described, as an example, in reference to the micro-pins 30, although other microstructures on the bottom 22 of the lens 12 or the bottom 26 of the holder 18 are contemplated in the scope of the present invention. After the contact lens 12 is placed on the cornea 32 of the eye 14 and centered, a surgeon applies downward pressure on the contact lens 12, which secures the lens 12 to the cornea 32. The micro-pins 30 extend through a tear film 34 on the surface of the cornea 32 and a viscous coupling agent (solution) used during the procedure when applied to the ocular surface of the eye.

The coupling fluids applied on the surface of the tear film 34 during the procedure may be selected from a group of coupling fluids such as 2% methocel, thiol-tears gel, 1.4% sodium hyaluronate, 0.9% simple saline, and other contact solutions applicable to the purposes of the ophthalmic care using contact lens.

The micro-pins 30 extend through the tear film 34 and the viscous solution film 36 on the surface of the cornea 32, and gently indent into the superficial cornea 32 without injuring it. A friction force is created between the lens' bottom surface and the coupling agent layer 36, as well as superficial corneal layer 32, by the micro-pins 30 indentation into the superficial cornea 32, so that the contact lens 12 or the contact lens holder 18 is temporarily anchored to the cornea 32 for the duration of the ophthalmic procedure. After the ophthalmic procedure has been completed, the contact lens 12 and/or the lens holder 18 is lifted from the eye 14.

Referring to FIGS. 1A and 2, the subject system 10 is also applicable for surgical gonioprism assembly 38 for glaucoma surgery, where a gonioprism contact lens 40 is used to obtain adequate visualization of the critical angle of the peripheral cornea to perform the micro invasive glaucoma surgery (MIGS) which includes implanting the stent or cutting into the trabecular meshwork. Glaucoma surgeons are generally opposed to placing fixation sutures during the glaucoma procedure in order to avoid trauma to the cornea or sclera of the eye. For this reason, the suture free system 38 of the current invention using a gonioprism contact lens 40 is highly desirable for use in ophthalmic procedures involving glaucoma surgical procedures.

As shown in FIG. 2, the gonioprism contact lens assembly 38 includes the gonioprism contact lens 40 and the lens holder 42. The bottom 44 of the lens holder 42 is formed with microstructure anchoring system 46 which may be in the form of micro-pins, micro-grips, micro-barbs, micro-needles or other textured elements formed on or attached to the bottom surface 44 of the lens holder 42. The details of the gonioprism assembly 38 will be presented in further paragraphs.

Referring to FIGS. 1A-1B, 3A-3B and 4A-4B showing the subject macular contact lens assembly 10, the contact lens 12 may be used by itself or in assembly with the lens holder 18. As presented in FIGS. 1A, 3A, and 4A, the contact lens 12 is used by itself. The contact lens 12 is equipped with the anchoring system 16 configured with microstructures 24 on the bottom 22. The micro-pins (or other microstructures) 30 are strategically placed on the bottom 22 of the lens 12.

Figure 3B:
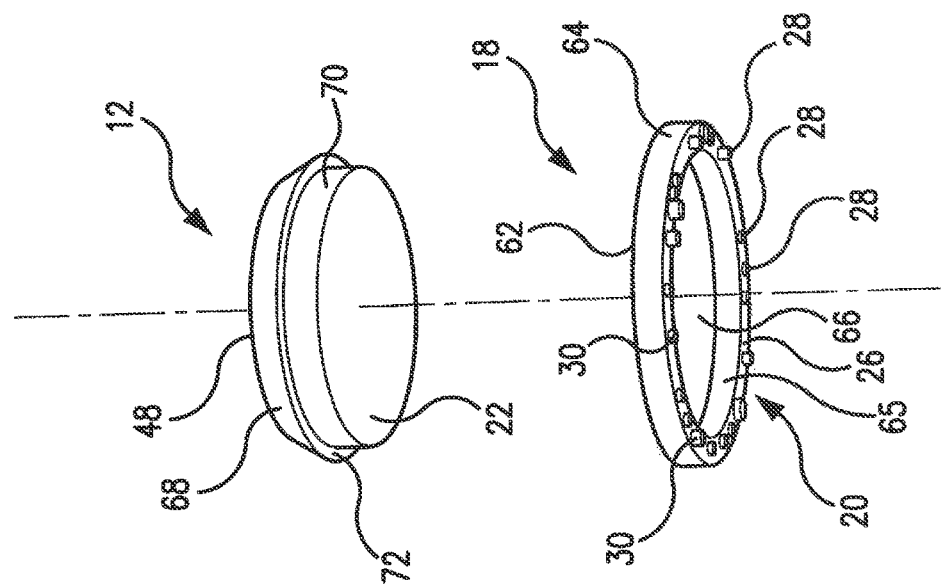
FIGS. 3B and 4B show an exploded view of the subject contact lens and contact lens/holder assembly showing micro structures formed on the bottom of the lens holder, where
Figure 3A:
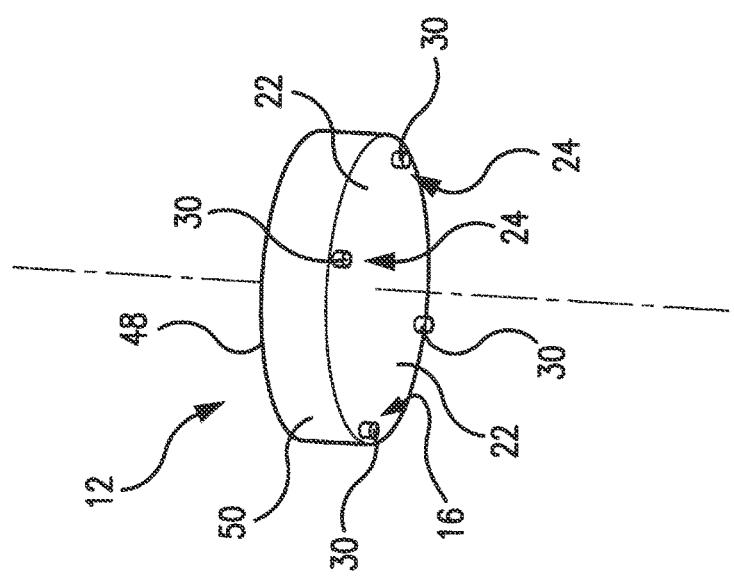
FIGS. 3A and 4A are representative of the subject macular contact lens, where
Figure 4B:
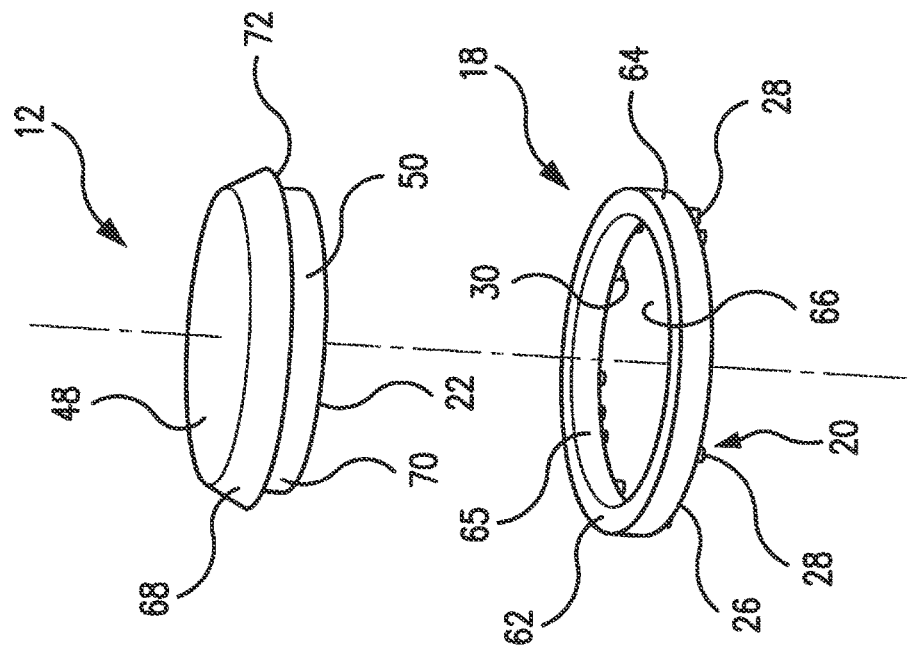
Figure 4A:
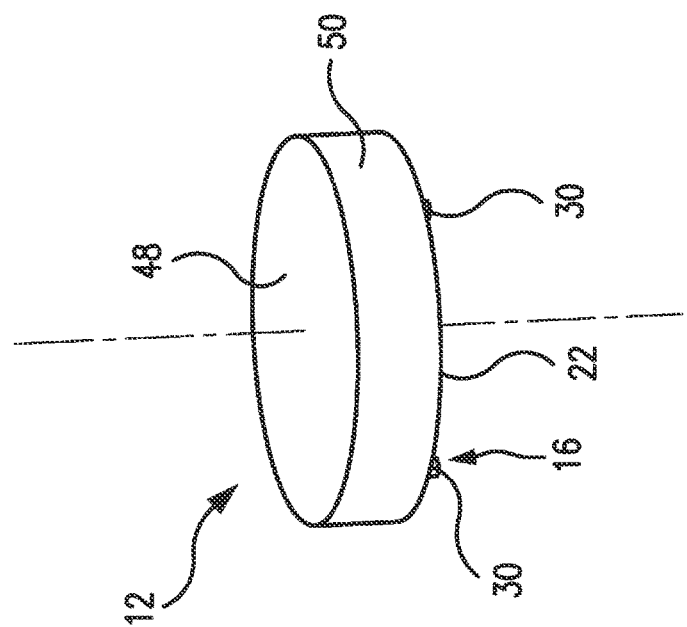

As shown in FIGS. 3A and 4A, the lens' bottom 22 is an eye contacting surface which may be shaped as a circular arc or in another suitable curved configuration to conform with the curvature of the eye cornea 32.

The lens 12 has the upper surface 48 spaced from the bottom surface 22 by circumferentially extending walls 50. The walls 50 of the contact lens 12 may form a cylindrical surface, trapezoidal surface, or other contoured surface as needed for specific optical properties of the lens 12. The upper surface 48 of the lens 12 may be smaller than, larger than, or of the same size with the surface of the bottom 22 of the lens 12 (as dictated by the needed optical properties of the lens 12).

The contact lens 12 may be manufactured from acrylic, glass, or other bio-compatible and optically viable materials used for the contact lens.

A number of micro structured elements 24 are provided on the bottom 22 of the lens 12. The function of the microstructures 24 is to provide friction between the bottom 22 of the lens 12 and the cornea 32 in order to prevent sliding of the lens 12 from the desired surgical site, as well as to anchor the lens in place when the microstructures 24 (for example micro-pins 30) penetrate through the viscous solution film 36 and tear film 34 and anchored to the superficial surface of the cornea 32.

A number of micro-pins 30 are shown on the bottom 22 of the lens 12 which constitutes an anchoring system 16. Although the number of micro-pins 30 shown in FIG. 3A on the bottom 22 of the lens 12 is four, any other number greater than two may be used and is contemplated within the scope of the subject invention.

The micro-pins 30 may be manufactured from surgical steel, bio-compatible plastics or polymers, for example, PEEK (polyether ether ketone), or other bio-compatible materials.

The micro-pins 30 may be manufactured integral with the bottom 22 of the contact lens 12 (for example, by 3-D printing), or may be attached to the bottom 22 of the lens 12 via numerous mechanisms, including, for example, but not limited to, drilling, pressing, threaded engagement, thermo-soldering, coupling with the help of bonding agents (glue, adhesive), various interlocking mechanisms, such as, for example, interlocking tab and groove locking mechanism, etc. The microstructures may also be formed by chemical etching, chemical vapor deposition, plasma machining, photolithography, and other applicable processes.

Figure 5A:
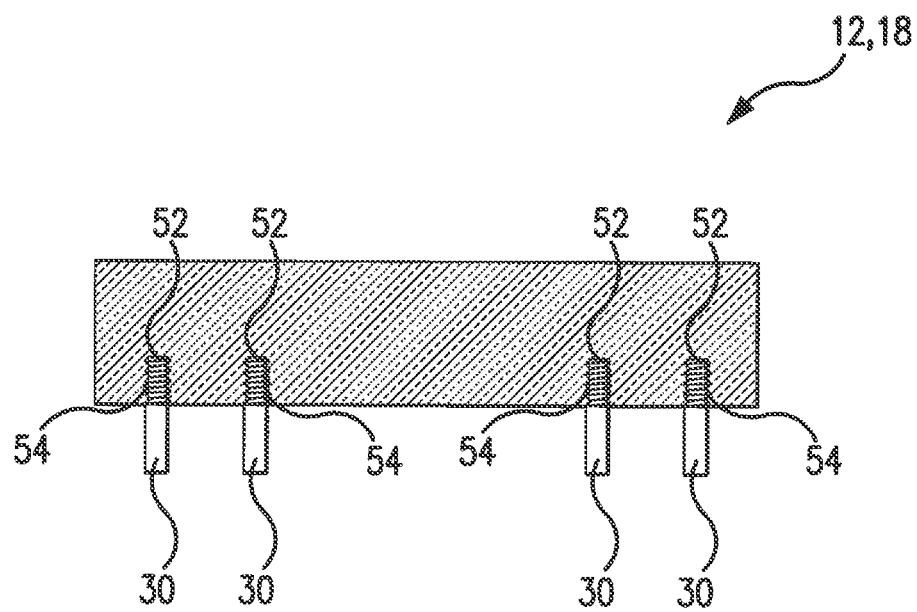
FIG. 5A shows a cross sectional view of the subject contact lens and contact lens/holder assembly showing microstructures threadingly engaged with the subject contact lens.
Figure 5B:
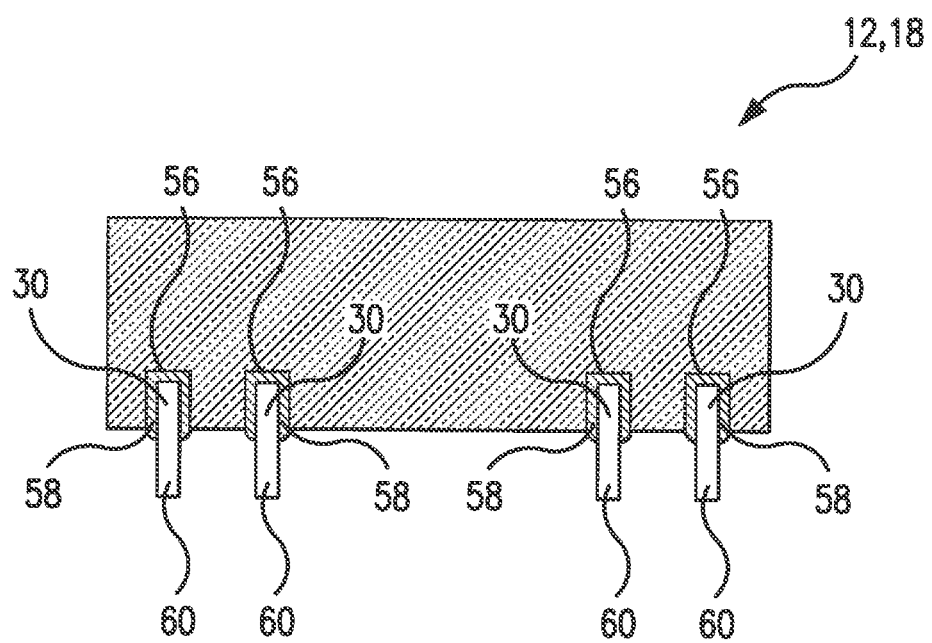
FIG. 5B shows a cross sectional view of the subject contact lens and contact lens/holder assembly showing microstructures fixedly engaged with the subject contact lens with a glue.

For example, as shown in FIG. 5A, openings 52 with the threaded walls 54 are pre-machined at the bottom 22 of the lens 12 to threadingly receive the micro-pins 30. Alternatively, as shown in FIG. 5B, the micro-pins can be glued in the openings 56 with glue 58 which may be, for example, a UV activated epoxy, or any other bio-compatible adhesive material.

Also alternatively to the drilling or gluing the micro-pins 30 into the bottom 22 of the lens 12, the lens with the micro-pins (or other microstructures contemplated in the present invention for the purposes of stabilization, centralization, and prevention of the slipping of the lens from the desired surgical site) may be formed by a 3-D printer from a bio-compatible plastic, or like composition, for example, PEEK material.

The preferred diameter of the micro-pins (in their cross-section) may be in the range of 0.0012 inch, and can protrude from the surface of the bottom 22 of the lens 12 approximately 0.0013 inch to extend through the tear film 34 and viscous solution film 36 into contact with the cornea 32. The micro-pins length from the bottom 22 to the exposed ends 60 thereof generally should not exceed 1 mm in order to prevent deep penetration into the cornea further than the corneal superficial layer.

The cross section of the micro-pins can be tapered down at the exposed ends 60 of the micro-pins 30, or squared off.

Although shown as the same shape and same length in FIGS. 3A and 4A, the microstructures 24 also can be made of different shape and different dimensions, for example, as shown in FIG. 3B.

Referring to FIGS. 1B, 3B and 4B, the ophthalmic contact lens assembly 10 of the present invention includes the lens 12 and the lens holder 18. In this arrangement, the stabilization, as well as centralization, of the ophthalmic contact lens system 10 at the desired site on the eye is provided by the anchoring system 20 configured on the bottom 26 of the lens ring holder 18. As shown, the annular bottom surface 26 of the lens holder 18 includes microstructures in the shapes of micro-pins 30, micro-grips, micro-barbs, micro-needles, or other textured micro-elements 24 positioned at a number of locations on the bottom 26 of the lens holder 18 around the periphery of the lens holder 18.

The annularly shaped contact lens holder 18 has an annularly shaped bottom 26 (with concentrically spaced apart inner and outer peripheral edges) and an annularly shaped upper surface 62 (with concentrically spaced apart inner and outer peripheral edges). The circumferential outside walls 64 extend between the outer peripheral edges of the bottom surface 26 and the outer peripheral edges of the upper surface 62.

Internal walls 65 extend between inner peripheral edges of the annularly shaped bottom surface 26 and upper surface 62, respectively, of the holder 18, and define a circularly shaped opening 66 therebetween.

The macular contact lens 12 is equipped with a flange element 68 which is formed integrally therewith or attached to the outer surface 70 of the circumferentially extending walls 50 of the lens 12. The flange element 68 has a flange 72 extending from the outer surface 70 of the circumferential extending walls 50 of the lens 12.

The bottom surface 22 of the lens 12 and the circumferentially shaped holder opening 66 of the lens holder 18 are shaped and dimensioned to correspond each to the other to permit the bottom 22 of the lens 12 to pass through the circumferentially shaped holder opening 66. The flange member 68 is positioned around the outer surface 70 of the circumferentially extending walls 50 of the lens 12 a distance from the bottom 22 of the lens 12 corresponding to the height of the walls 64 of the lens holder 18 between the bottom surface 26 and the upper surface 62 thereof. When the contact lens 12 is received in the holder opening 66 of the lens holder 18, the flange 72 of the flange member 68 is supported by the annularly shaped upper surface 62 of the lens holder 18, thus preventing the contact lens 12 from displacing its bottom surface 22 below the bottom surface 26 of the lens holder 18.

During the procedure, the lens ring holder 18 is positioned over the cornea 32, and the lens 12 is received in the holder opening 66 of the lens holder 18. The surgeon gently pushes down the contact lens/holder assembly 10, so that the microstructures 28 on the bottom surface 26 of the lens holder 18 penetrate through the tear film 34 and viscous solution film 36 (as shown in FIGS. 1B and 2) and into the contact with superficial layer of the cornea 32 to gently indent into the cornea 32 without traumatizing the eye tissues to provide stabilization and centralization of the contact lens/holder assembly 10 in place and to prevent the deviation of the assembly 10 from the desired position during the ophthalmic procedure.

The lens ring holder 18 may be formed from polyether ether ketone (PEEK) material, or any other compound which is bio-compatible and capable of holding the contact lens 12 in position.

The height of the walls 64 of the lens holder 18 may be in the range of 1-2 mm, with the holder opening diameter ranging from 9 to 15 mm, for example, 11.5 mm.

The microstructures 28, for example, micro-pins 30, are formed along the circumference of the annularly shaped bottom 26 of the lens holder 18 in any manner similar to that described in previous paragraphs for the anchoring system 16 on the bottom 22 of the contact lens 12.

A number of the micro-pins 30 on the bottom 26 of the lens holder 18 may range from 2 to 25 depending on the friction needed between the lens holder 18 and the tissues of the eye.

It has been experimentally concluded that the microstructures 24, 28 can extend from the bottom of the lens 12 or from the bottom of the lens holder 18 no more than 1 mm in order to prevent excessive penetration and possible trauma to the surface of the tissues of the eye under surgery.

Figure 7B:
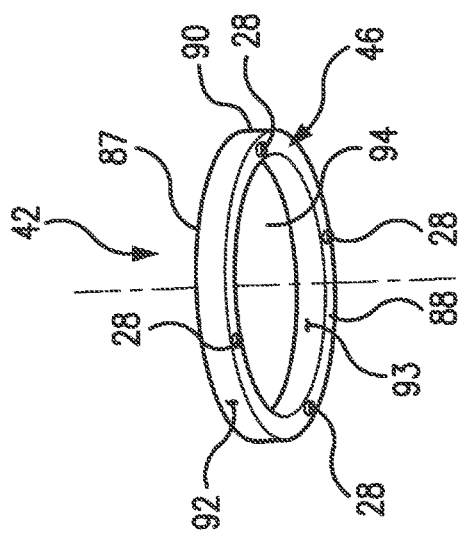
Figure 6B:
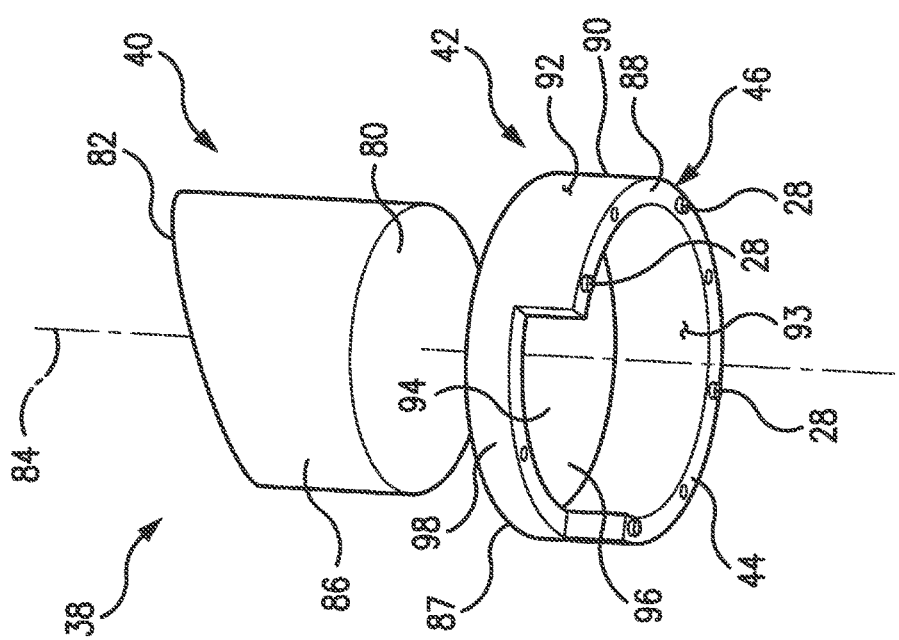

Referring to FIGS. 6A and 6B, as well as FIGS. 7A and 7B, the gonioprism assembly 38 includes a gonioprism contact lens 40 having a bottom surface 80 which is a circularly shaped surface configured to comply with the curvature of the eyeball. The gonioprism contact lens 40 has an upper surface 82 which is oval shaped and tilted as inclined with respect to the longitudinal axis 84 of the gonioprism contact lens 40. Walls 86 extend in cylindrical contoured configuration between the edges of the bottom surface 80 and upper surface 82 of the gonioprism contact lens 40.

The lens holder ring 42 includes an upper annularly shaped surface 87 and a bottom surface 88 which extend each from the other by a predetermined distance 90 defined by circumferentially shaped outer walls 92 of the gonioprism lens holder ring 42. The outer walls 92 extend between the outer peripheral edges of the annularly shaped upper and bottom surfaces 87, 88, respectively.

The lens holder ring 42 further has inner walls 93 which extend circumferentially between inner peripheral edges of the annularly shaped upper and bottom surfaces 87, 88, respectively.

The inner walls 93 are contoured with a cylindrically shaped surface and define a holder opening 94 therebetween. The holder opening 94 in the lens holder ring 42 is shaped and dimensioned to correspond to the bottom surface 80 of the gonioprism contact lens 40.

The circumferentially shaped outer walls 92 and inner walls 93 may be configured with an incision access cut-out 96 which may be a partial cut-out with a connecting element 98 extending along the edge of the upper surface 86 of the lens holder ring 42.

Alternatively, as shown in FIGS. 7A and 7B, the lens holder ring 42 for the gonioprism assembly 38 may be similar to the lens holder 18 shown in FIGS. 3B and 4B formed as an annularly shaped lens holder with an opening 94 shaped and dimensioned for passing the bottom 80 of the gonioprism contact lens 40.

In the arrangement shown in FIGS. 6A and 6B, the partial cut-out 96 is formed for surgical access/entry and visualization of the corneal incision. This cut-out 96 is positioned in relation to the site of the surgery so that the cut-out 96 is stabilized over the corneal or cataract incision. The modification of the gonioprism contact lens assembly 38 shown in FIGS. 6A and 6B permits the surgeon to view the incision site and to guide the surgical instrument into the anterior chamber of the eye for the ophthalmic surgery such as glaucoma surgery.

In the gonioprism assembly 38, shown in FIGS. 6A-6B and 7A-7B, the bottom surface 88 of the lens holder ring 42 is provided with microstructured anchoring system 46 which, similar to that provided at the bottom 22 of the contact lens 12 and the bottom 26 of the lens ring holder 18 shown in FIGS. 1A-1B, 3A-3B and 4A-4B, is manufactured with microstructures 28, described in previous paragraphs.

Figure 8A:
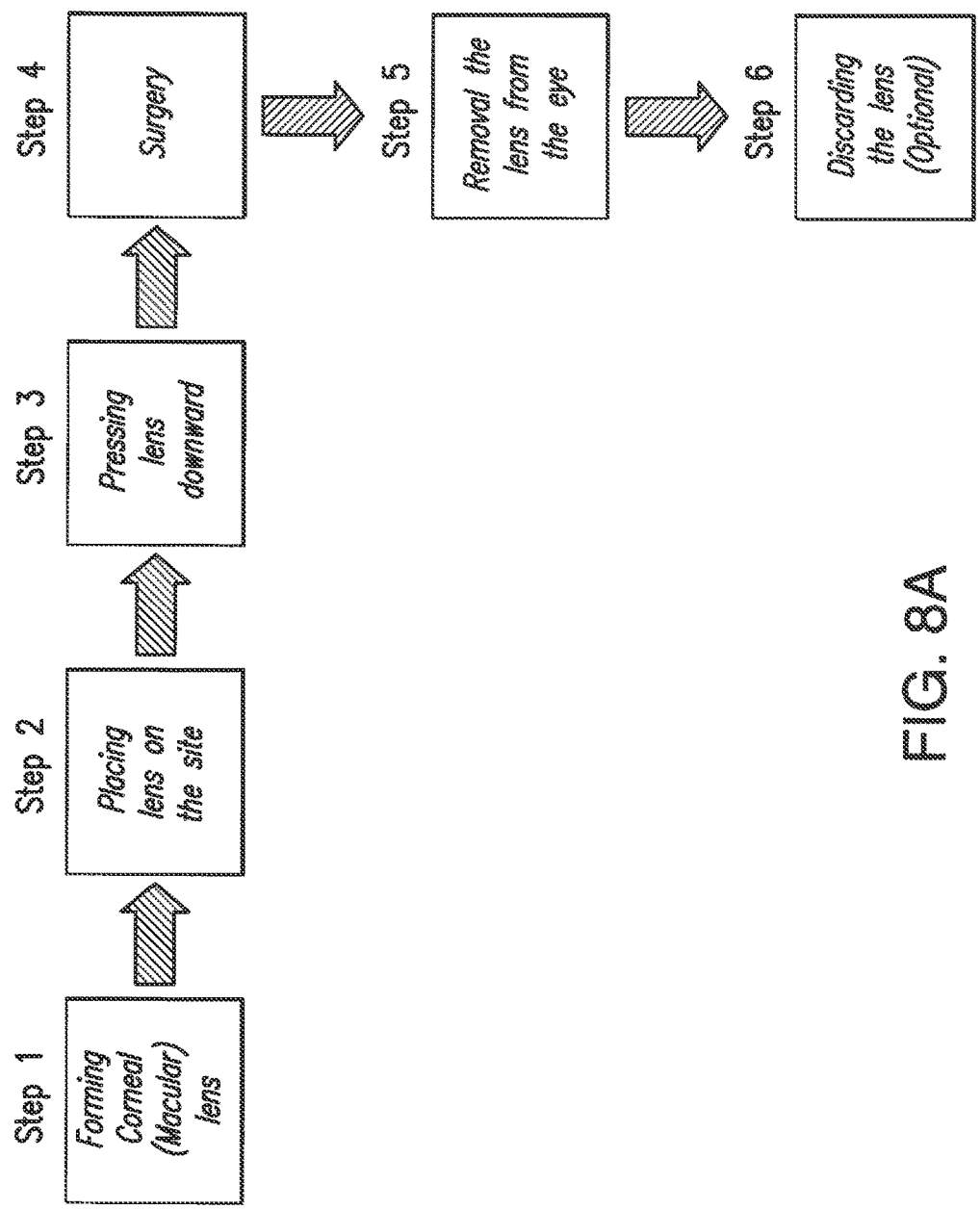
FIGS. 8A-8B represent the steps of the subject surgical procedure using the subject contact lens assembly with the macular (corneal) contact lens (FIG. 8A) and with the gonioprism contact lens assembly (FIG. 8B).

Referring to FIG. 8A, representative of the ophthalmic procedure supported by the use of the subject non-sliding, non-sutured hands-free contact lens anchoring assembly, the method begins in Step 1, wherein the subject corneal (macular) contact lens assembly is formed which includes either the contact lens or the contact lens and the lens ring holder, where either the bottom of the lens is configured with the microstructure anchoring system or the bottom of the ring holder is configured with the anchoring microsystem. When the subject contact lens assembly is formed in Step 1, the method advances to Step 2 where either the subject contact lens with the anchoring system on the bottom thereof, or the lens ring holder with the microstructured anchoring system on the bottom thereof is positioned above the desired surgery site on the eye.

From Step 2, the operation follows to Step 3, where a surgeon gently presses down either the contact lens to provide that the exposed ends of the micro-pins penetrate through the tear film and the viscous solution film, and in contact with superficial layer of the cornea.

In the procedure which uses the assembly of the contact lens and the lens ring holder, the contact lens is lowered into the opening of the lens ring holder. In both situations, the bottom of the contact lens comes into contact with the viscous solution film (when the solution is used for the procedure) or with the tear film.

In the following Step 4, the surgeon performs the ophthalmic procedure such as vitreoretinal surgery or macular surgery. During the procedure, the subject contact lens assembly allows the surgeon to visualize the macular and other structures of the eye in high magnification. The contact lens assembly remains stabilized and centered on the cornea of the eye and is prevented from slipping from the desired surgical site.

Upon completion of the surgery procedure in Step 4, the surgeon lifts the contact lens assembly from the eye, thus disengaging the microstructures from the tissues of the eye. The tissues of the eye are not traumatized by the micro-pins engagement therewith.

Following Step 5, the subject assembly may be discarded (optionally) or sent for disinfection for use in other procedures.

During the Step 4, the surgery is performed in a hands-free manner, when the surgeon (or the surgeon's assistant) does not have to manually locate and relocate the contact lens assembly. Non-sutured stabilization and centralization of the subject contact lens assembly and prevention from sliding from the desired surgical site is provided in the present method by the subject anchoring system formed at the bottom of the lens or at the bottom of the lens ring holder.

Figure 8B:
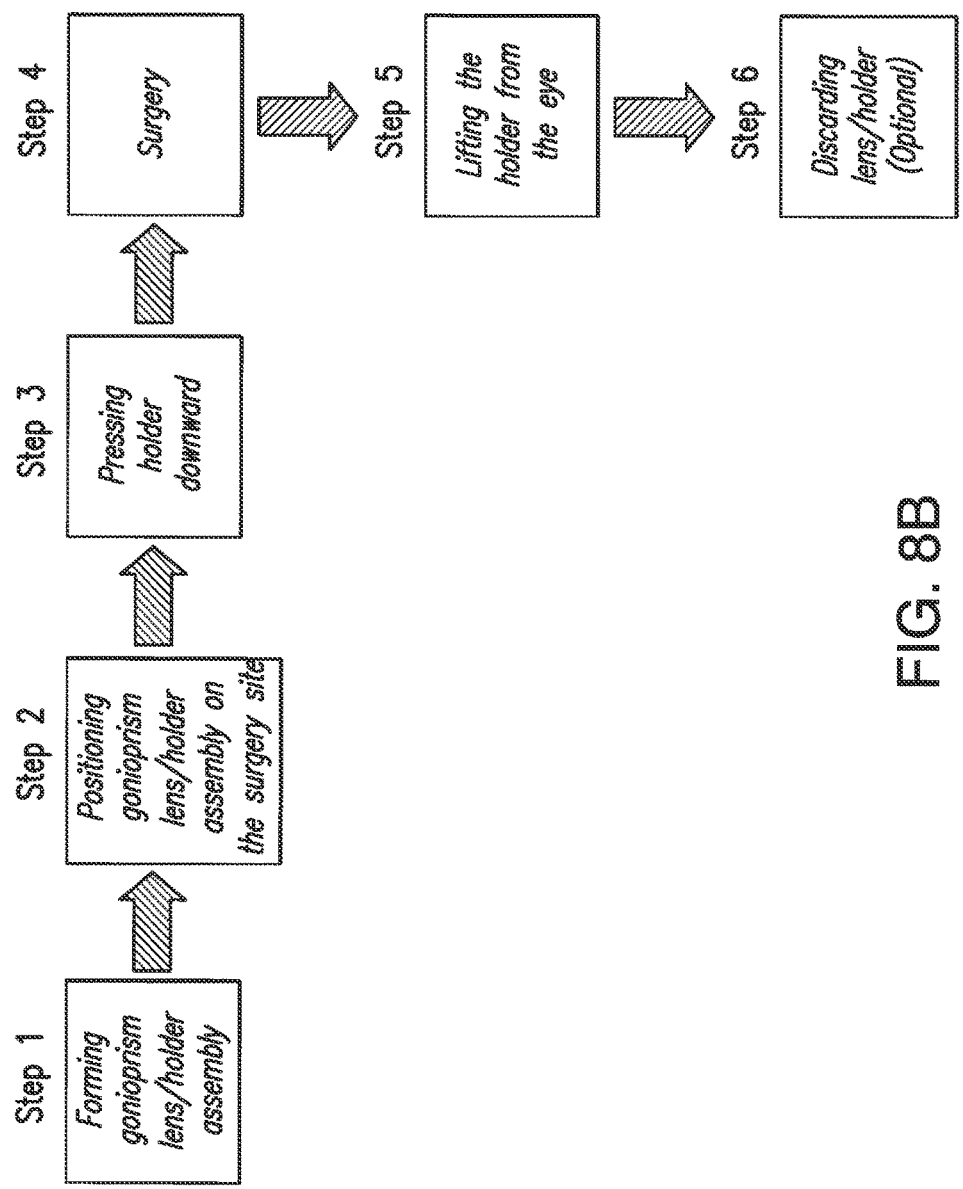

Referring to FIG. 8B, in Step 1, the gonioprism assembly is formed which includes a gonioprism contact lens and the lens holder ring, where a microstructured anchoring system is formed on the bottom of the lens holder ring.

Following Step 1, the surgeon places the lens holder ring of the gonioprism assembly on the site of the surgery, lowers the gonioprism contact lens into the holder opening of the lens holder ring, and in Step 3 gently presses the lens holder ring down into the eye so that the exposed ends of the micro-pins (or other microstructures contemplated in the scope of the present invention) penetrate through the tear film and the viscous solution film of the eye as shown in FIG. 2, and are in contact with a superficial layer of the eye tissue.

In Step 2, the cut-out is positioned over the site of the corneal or cataract incision.

In the following Step 4, the surgery (such as, for example, micro-invasive glaucoma surgery) is performed. During the surgery, the surgeon uses the subject gonioprism assembly in a hands-free manner without the need of stabilization and centralization of the gonioprism assembly by sutures. The sliding of the gonioprism assembly from the site of the surgery is prevented by the friction force provided by the microstructure on the bottom of the lens holder ring.

Upon completion of the surgery in Step 4, the surgeon lifts the lens holder ring form the eye, thus disengaging the exposed ends of the microstructures on the bottom surface of the lens holder ring from the eye's tissues.

In Step 6, following the removal of the gonioprism assembly from the eye, the gonioprism assembly can be optionally discarded or sent for cleaning and treatment for possible use in other procedures.

During an opthalmic procedure, it is important that that the contact lens be maintained in a stable, non-moveable positional location as the surgeon is operationally proceeding. In some cases the patient may tilt his/her head with a responsive tilting of the contact lens holder and the contact lens. This tilting causes unwanted gravitational assist forces to be applied to the contact lens and the contact lens holder which may, in some cases permit a displacement of the contact lens from the intended site.

Figure 9:
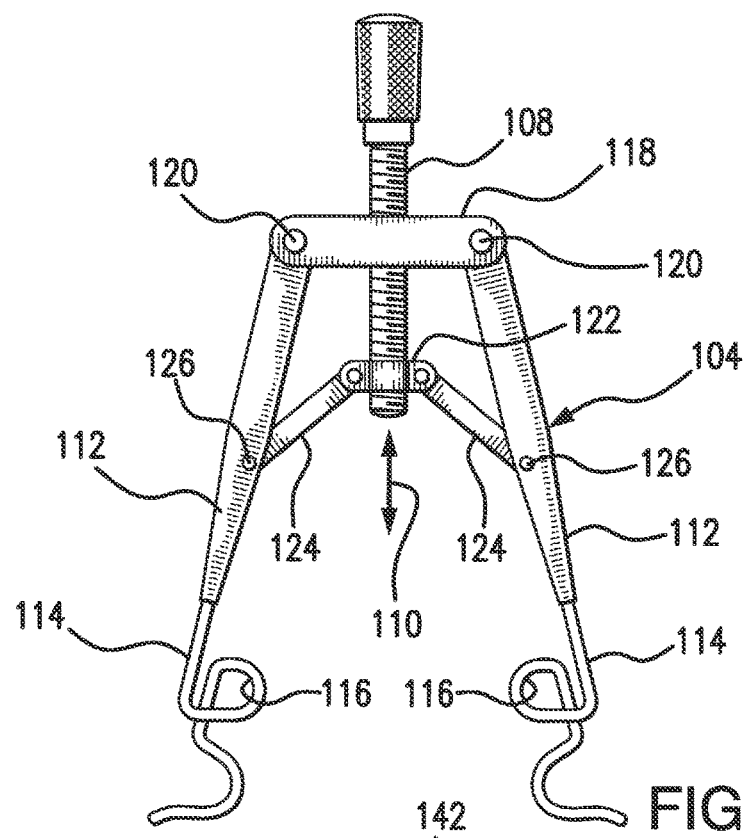
FIG. 9 is a frontal elevation view of an eye speculum used in conjunction with the subject contact lens and contact lens holder.
Figure 10:
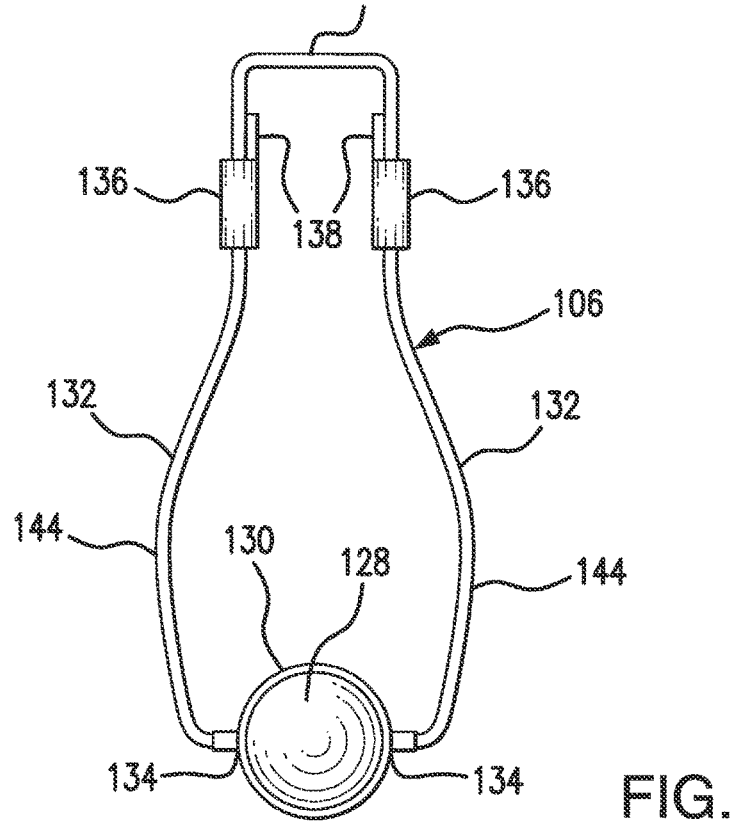
FIG. 10 is frontal elevational view of a stabilization mechanism to be coupled to the eye speculum as seen in FIG. 9.
Figure 11:
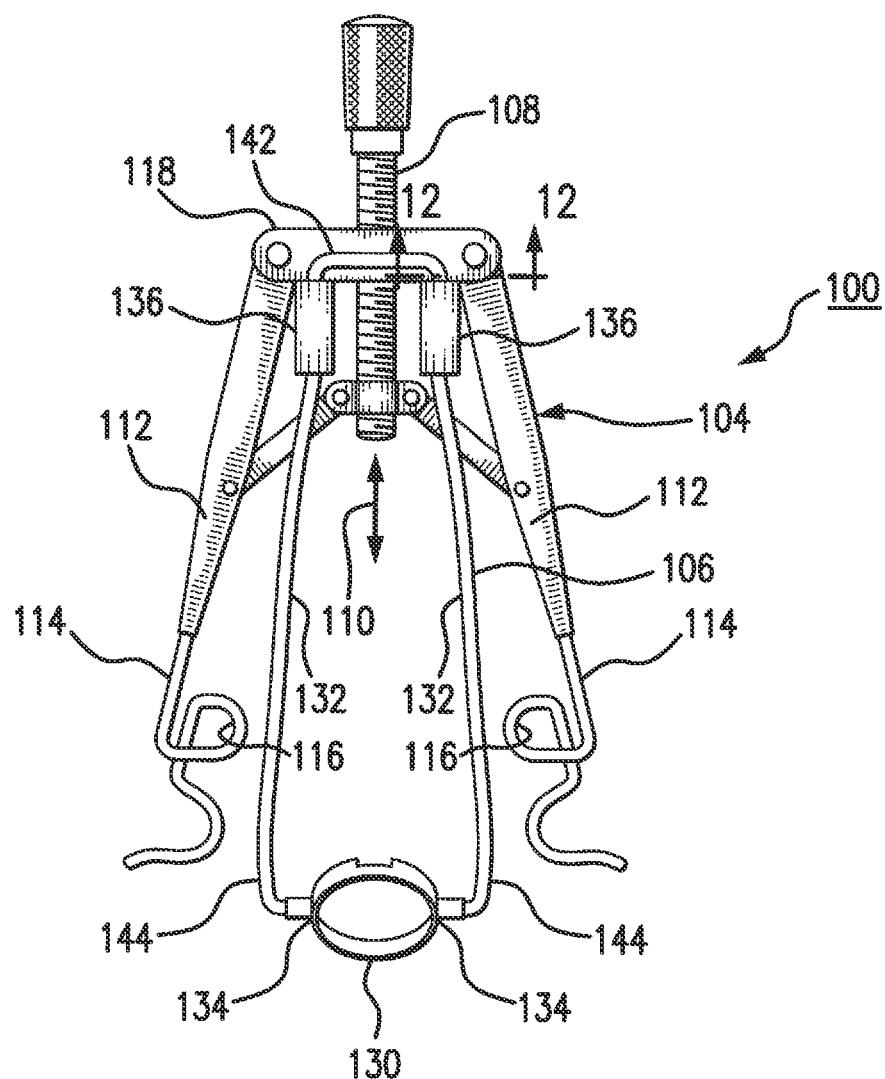
FIG. 11 is a frontal elevational view of the speculum assembly showing the stabilization mechanism in assembly with the speculum; and, FIG. 12 is a cross-sectional view partially cut-away showing the sleeve member appendage inserted within a plate member of the speculum.

Referring now to FIGS. 9-12, there is shown a speculum assembly 100 to add further stabilization and non-displaceabilty of the contact lens 128 and the contact lens holder 130 which is seen in the operational combination in FIG. 11.

The contact lens assembly of 100 includes a speculum of 104 seen in FIGS. 9 and 11. Contact lens assembly or speculum assembly 100 includes speculum 104 and stabilization mechanism 106 to be further described in following paragraphs. Speculum or eye speculum 104 may be a standard eyelid speculum used for ophthalmic procedures which is commercially available and commonly known in the art. Speculum 104 may be of the type of that is commonly known as a "Lieberman eyelid speculum", although other speculums may be used in conjunction with stabilization mechanism 106. For purposes of clarity and ease of understanding the "Lieberman" speculum will be used in further description.

Speculum 104 includes threaded member 108 for threaded engagement with plate member 118 of speculum 104. Operationally, threaded member 108 may be rotationally displaced to displace threaded member 108 in a linear direction coincident with axis line 110. A lower section (as seen in FIG. 9) of threaded member 108 is coupled to bracket 122 which is reversibly displaceable along axis line 110. Bracket 122 is pivotally connected to intermediate arm members 124 positioned on opposing sides of bracket 122 as is seen in FIG. 9.

Intermediate arms 124 are respectively pivotally connected at pivots 126 to speculum arm members 112. Speculum arm members 112 are pivotally coupled to plate member 118 on opposing horizontally displaced ends to permit radial displacement of speculum arm members 112 responsive to the rotation of threaded member 108.

In this manner, rotation of threaded member 108 which is in threaded engagement with plate member 118 causes a linear displacement in axis direction 112 of bracket member 122. Displacement of bracket member 122 being pivoted to intermediate arm members 124 which are in themselves pivoted being radially displaceable.

Loop members 114 are fixedly connected to respective speculum arm members 112 as shown. Loop members 114 are operationally used for bearing against the patient's eyelids to maintain the patient's eyelids displaced each from the other during the ophthalmic procedure. As speculum arm members 112 are radially displaced away from each other there is a respective displacement of loop members 114 away from each other. As previously described loop members 114 are adapted to contact opposing eye lids of a patient during the medical procedure and maintain the patient's eyelids in a relatively stable and spaced position.

Loop members 114 are generally wire members composed of a biocompatible solid material which has some flexibility such as stainless steel or some like composition not important to the inventive concept as herein described with the exception that loop members 114 are capable of accepting the loads imposed thereon.

Contact lens assembly 100 includes contact lens 128 which may in some cases be in the form of a geoprism lens as shown in FIG. 10. Contact lens holder 130 as seen in FIGS. 10 and 11 is secured to a contact lens 128 through adhesive bonding or some other like technique. Contact lens holder 130 is fixed to contact lens 128 at least partially along a periphery of contact lens 128. In this manner contact lens holder 128 is fixedly attached to contact lens 128. The function of contact lens holder 130 is to provide support and stabilization of contact lens 128 when contact lens 128 is positioned over a medical procedure site of a patient's eye.

Contact lens 128 may be of the type previously described in FIG. 3A-4B. Contact lens 128 may include the anchoring mechanisms previously described to retain contact lens 128 at the selected procedure site during the ophthalmic procedure. Such an anchoring mechanism as previously described may include a plurality of microstructures located on the bottom surface of wall contact lens 128. These microstructures may be selected from the group of micro-pins, micro-grips, micro-barbs, micro-needles, textured micro-elements as well as combinations thereof.

As described, contact lens holder 130 is fixedly secured to contact lens 28 throughout or at least a portion of the periphery of contact lens 130 as is seen in FIG. 10. Contact lens holder 130 may be formed of a polygonal or circular cross-sectional contour tubing for matingly interfacing with contact lens 128. As shown in FIGS. 10 and 11 contact lens holder 130 is formed by a substantially cylindrical tubing which receives contact lens 128. However, the particular contour of contact lens holder 130 is not important to the inventive concept as herein described with the exception that it is adhered to at least a portion of contact lens 128 in order to securely hold contact lens 128 within contact lens holder 130. Contact lens holder 130 may be composed of a solid composition which is bio-compatible, such as stainless steel or some like composition which is substantially rigid.

As more clearly seen in FIG. 10, stabilization mechanism 106 includes flexible stabilization wire 132 having a stabilizing wire first ends 134 secured to contact lens holder 130 on opposing sides of lens holder 130 as is shown in both FIGS. 10 and 11. Stabilizing wire first ends 134 may be adhered to lens holder 130 by adhesion or some like technique with the important consideration being that lens holder 130 is secured to stabilizing wire 132 at stabilizing wire first ends 134. When taken in combination, contact lens 128, contact lens holder 130, and flexible stabilizing wire 132 form a closed contour.

Stabilizing wire 132 passes through a pair of sleeve members 136 which are mounted to and on opposing sides of stabilizing wire 132 which is clearly seen in FIG. 10. Each of sleeve members 136 is formed of either an elastic composition such as rubber or in fact may be a formed of a bio-compatible composition which may be rigid. For purposes of illustration, sleeve member 136 is shown as being a substantially tubular contour. Sleeve members 136 are fixedly attached to stabilizing wire 132 by adhesive attachment or some like mechanism not important to the inventive concept as herein described. Each sleeve member 136 includes a respective sleeve member appendage or lug 138 extending from end of each of sleeve members 136 in the axial direction 110. Sleeve member appendages 138 are fixedly secured to sleeve members 136 by being formed in one-piece formation with the sleeve members 136 or otherwise fixedly attached to respective sleeve members 136.

Each end of plate member 118 is formed with a recess 140 within which respective speculum arm members 112 are pivotally connected as previously described. Thus the ends of plate member 118 take the form of a C-shape which provides a space between the speculum arm members 112 and the body of plate member 118.

Figure 12:
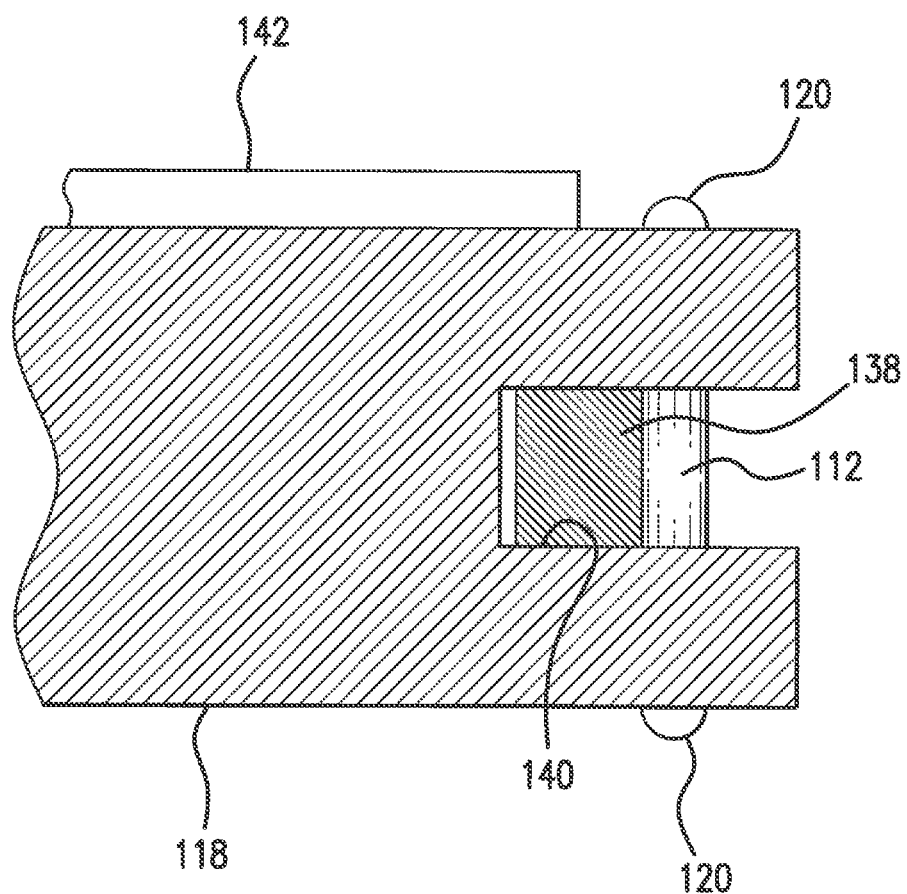

Sleeve member appendages 138 extending from an end of each of sleeve members 136 are insertable within opening or recess 140 of plate member 118 as seen in FIG. 12. Sleeve member appendages 138 are inserted within plate opening 140 and may be wedged within plate opening 140 or otherwise secured thereto. In one aspect of system 100, appendages or lugs 138 are frictionally secured within recesses 140 to permit easy removal of stabilizing mechanism 106 from eye speculum 104 subsequent to the ophthalmic procedure. Stabilizing wire 132 includes stabilizing wire upper section 142 and is adapted to extent over an upper surface of plate member 118 in a direction perpendicular to axis direction 110.

In this manner there is formed a continuous stabilizing wire 132 contour extending from stabilizing wire first ends 134 to provide a continuous stabilizing wire 132 between stabilizing wire first ends 134 as is seen in both FIGS. 10 and 11. Stabilizing wire 132 includes a lower stabilizing wire section which passes between loop members 114 having inner loop sections 116 as is seen in assembly in FIG. 11.

Operationally, when threaded member 108 is rotated, respective intermediate arm members 124 radially displace speculum arm members 112. Stabilizing wire 132 is mounted within speculum arm members 112, as is seen in FIG. 11 in operational combination. Stabilizing wire 132 is thus secured to eye speculum 104 between the displacement distance of inner loop sections 116 and may be essentially independent of the displacement of speculum arm members 112.

Stabilizing wire 132 is fabricated from a malleable material such as stainless steel, a plastic composition or some like material which can hold its shape in a stable mode, but can be bent or flexibly displaced.

In this manner during an ophthalmic procedure, contact lens holder 130 and captured contact lens 128 are lowered onto the predetermined location desired in cooperation with the eye speculum 104 If adjustments are needed to the positioning of lens holder 130, the surgeon can simply apply pressure to a mid-section of stabilizing wire 132 to effect displacement of lens holder 130 and associated contact lens 128. The adjustment pressure on stabilizing wire can be accomplished by the surgeon applying displacement force to the stabilizing wire 132 through the use of forceps contacting and applying pressure to opposing sides of stabilizing wire 132.

In this manner, when a patient during a medical procedure tilts his/her head, the contact lens holder 130 and responsively the contact lens 128 are maintained in a stabilized position which acts against any gravity assist forces which may be encountered during the opthalmic procedure.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of the elements may be reversed or interposed, all without departing from the spirit or scope of the invention as defined in the appended claims.

What is being claimed is:

1. A contact lens assembly for ophthalmic procedures, comprising:
    an optical element having a bottom eye contact surface, an upper surface, and side walls extending circumferentially between an edge of said bottom eye contact surface and an edge of said upper surface;
    an annularly contoured optical element holder configured with:
    an annularly shaped bottom surface having inner and outer concentrically spaced apart edges,
    an annularly shaped upper surface having inner and outer concentrically spaced apart edges,
    outer walls extending circumferentially along and between said outer edges of said annularly shaped bottom and upper surfaces, respectively, of said annularly contoured optical element holder, and
    internal walls extending circumferentially along and between said inner edges of said annularly shaped bottom and upper surfaces, respectively, of said annularly contoured optical element holder and defining a holder opening therebetween, said holder opening being shaped and dimensioned in correspondence to said bottom eye contact surface of said optical element; and
    an anchoring mechanism formed at and integrally with said annularly shaped bottom surface of said annularly contoured optical element holder, said anchoring mechanism being configured with microstructures disposed at predetermined positions on said bottom surface of said annularly contoured optical element holder, wherein, when said annularly contoured optical element holder is placed on a procedure site on the eye, said microstructures extend vertically downward from said annularly shaped bottom surface of said annularly contoured optical element holder into contact with tissues of the eye at said procedure site, thus creating an anchoring action for said annularly contoured optical element holder at said procedure site.

2. The contact lens assembly for ophthalmic procedures of claim 1, wherein said optical element is selected from the group of a corneal lens or a gonioprism contact lens.

3. The contact lens assembly for ophthalmic procedures of claim 1, wherein said optical element is received in said holder opening of said annularly contoured optical element holder and maintained with said bottom eye contact surface in contact with the tissues of the eye at said procedure site by said annularly contoured optical element holder anchored at said procedure site by said anchoring mechanism formed on said bottom surface of said annularly contoured optical element holder.

4. The contact lens assembly for ophthalmic procedures of claim 1, wherein said microstructures of said anchoring mechanism include at least one microstructure selected from a group consisting of: micro-pins, micro-grips, micro-barbs, micro-needles, textured micro-elements, and combinations thereof.

5. The contact lens assembly for ophthalmic procedures of claim 1, wherein said microstructures extend from said eye contact surface a length less than 1 mm.

6. The contact lens assembly for ophthalmic procedures of claim 1, wherein said microstructures are attached to said eye contact surface by mechanism selected from the group of: threaded connection, adhesion, gluing, pressing, thermo-soldering, 3-D printing, and combinations thereof.

7. The contact lens assembly for ophthalmic procedures of claim 1, wherein said microstructures are fabricated from a material selected from the group of: surgical steel, bio-compatible plastic, polyether ether ketone (PEEK) polymer, and combinations thereof.

8. The contact lens assembly for ophthalmic procedures of claim 1, wherein said outer walls of said annularly contoured optical element holder are shaped with a cut-out portion extending a predetermined length along said outer walls for surgical tools access and visualization of said desired procedure site.

9. The contact lens assembly for ophthalmic procedures of claim 1, wherein said annularly contoured optical element holder is fabricated from a material selected from the group of: surgical steel, bio compatible plastic, polyether ether ketone (PEEK) polymer, and combination thereof.

10. The contact lens assembly for ophthalmic procedures of claim 1, wherein said optical element further includes a flange member formed on said side walls thereof, said flange member having a flange portion extending circumferentially along the perimeter of said side walls and extending therefrom a predetermined distance corresponding to a width of said annularly shaped upper surface of said annularly contoured optical element holder between said inner and outer edges thereof, wherein, when said optical element is received in said holder opening, said flange portion being positioned in contact with and is supported by said annularly shaped upper surface of said annularly contoured optical element holder, thus restricting a downward displacement of said optical element relative said annular contoured optical element holder.

11. A method of performing an ophthalmic procedure, comprising:
    a. configuring a contact lens assembly comprising:
    a contract lens having a bottom eye contact surface, and sidewalls extending circumferentially between an edge of said bottom eye contact surface and an edge of said upper surface,
    an annularly contoured lens holder having an annularly shaped bottom surface, an annularly shaped upper surface, outer walls extending circumferentially along and between outer edges of said annularly shaped bottom and upper surfaces, respectively, of said annularly contoured lens holder, and internal walls extending circumferentially along and between inner edges of said annularly shaped bottom and upper surfaces, respectively, of said annularly contoured lens holder and defining a holder opening therebetween, said holder opening being shaped and dimensioned in correspondence to said bottom eye contact surface of said lens, and an anchoring mechanism disposed on either said bottom eye contact surface of said contact lens or on said annularly shaped bottom surface of said annularly contoured lens holder, and formed integrally therewith, said anchoring mechanism being configured with microstructures extending vertically downward from said bottom eye contact surface of said contact lens or from said annularly shaped bottom surface of said annularly contoured lens holder;

b. placing said contact lens assembly over said procedure site;

c. pressing said contact lens assembly downward to attain contact between said microstructures and the tissues of the eye at said procedure site, thus creating an anchoring action for said contact lens at said procedure site;

d. performing said ophthalmic procedure; and e. upon completion of said ophthalmic procedure, lifting said contact lens assembly from the eye.

12. A contact lens assembly for ophthalmic procedures, comprising:

an eye speculum adapted for displacing the eyelids of a patient, said eye speculum having a threaded member extending in axial direction for radially displacing a pair of speculum arm members and a plate member pivotally fastened to said speculum arm members at respective ends of said plate member;

a contact lens adapted for contacting an eye of said patient;

a contact lens holder secured to said contact lens;

an anchoring mechanism disposed on an eye contact surface of either of said contact lens and said contact lens holder and formed integrally therewith;

a stabilization mechanism secured to said contact lens holder and said eye speculum for stabilizing said contact lens at a predetermined positional location during said ophthalmic procedure, said stabilization mechanism including a stabilizing wire secured, at an upper stabilizing wire section thereof, to said plate member, and having first and second ends, at a lower stabilizing wire section thereof, secured to said contact lens holder at opposing sides thereof; and wherein said lower stabilizing wire section is formed of a malleable wire composition which may be displaced for adjustment of said contact lens and said contact lens holder positional placement.

13. The contact lens assembly as recited in claim 12 where said anchoring mechanism is configured for retaining said contact lens at a selected procedure site during said ophthalmic procedure.

14. The contact lens assembly as recited in claim 13 where said anchoring mechanism includes a plurality of microstructures disposed on a bottom surface of said contact lens.

15. The contact lens assembly as recited in claim 14 where said microstructures include at least one microstructure selected from the group of micro-pins, micro-grips, micro-barbs, micro-needles, textured micro-elements, and combinations thereof.

16. The contact lens assembly as recited in claim 12 where said contact lens holder is fixedly secured to said contact lens at a periphery of said contact lens.

17. The contact lens assembly as recited in claim 16 where said contact lens holder is formed of a substantially cylindrical tubing for receiving said contact lens.

18. The contact lens assembly as recited in claim 17 where said contact lens holder is adhered to said contact lens at at least a portion of said contact lens periphery.

19. The contact lens assembly as recited in claim 12 where said eye speculum includes a pair of loop members extending from said respective speculum arm members being adapted to displace said patient's eyelids, said loop members being displaced each from the other for maintaining said patient's eyelid in a stable displaced position.

20. The contact lens assembly as recited in claim 19, where said stabilization mechanism further includes:

a pair of sleeve members contiguous said eye speculum plate member, each of said sleeve members having a through passage for insert therethrough of said stabilizing wire.

21. The contact lens assembly as recited in claim 20 where each of said sleeve members includes a tubular contour having respective appendages extending from respective ends thereof.

22. The contact lens assembly as recited in claim 21 where said respective sleeve appendages are insertable within openings formed on opposing sides of said plate member and securable thereto.

23. The contact lens assembly as recited in claim 22 where said upper stabilizing wire section of said stabilizing wire extends external said respective sleeve members along an outer surface of said plate member between said sleeve members.

24. The contact lens assembly as recited in claim 23 where said lower stabilizing wire section of said stabilizing wire passes between said respective loop members and secured to opposing sides of said contact lens holder for holding said contact lens holder in a predetermined positional location when said speculum arm members are radially displaced.

* * * * *